United States Patent
Blancke et al.

(10) Patent No.: US 11,235,300 B2
(45) Date of Patent: Feb. 1, 2022

(54) PRETREATMENT PROCESS FOR IMPROVING THE FILLING OF A CHAMBER WITH SOLID PARTICLES

(71) Applicant: IFP Energies nouvelles, Rueil-Malmaison (FR)

(72) Inventors: Guillaume Blancke, Francheville (FR); Morgane Josserand, Lyons (FR); Danielle Richard, Lyons (FR); Catherine Laroche, Vernaison (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 0 days.

(21) Appl. No.: 16/956,998

(22) PCT Filed: Nov. 30, 2018

(86) PCT No.: PCT/EP2018/083126
§ 371 (c)(1),
(2) Date: Jun. 22, 2020

(87) PCT Pub. No.: WO2019/120938
PCT Pub. Date: Jun. 27, 2019

(65) Prior Publication Data
US 2020/0330942 A1    Oct. 22, 2020

(30) Foreign Application Priority Data
Dec. 21, 2017    (FR) ...................................... 1762784

(51) Int. Cl.
*B01J 2/00* (2006.01)
*B01J 2/30* (2006.01)
(Continued)

(52) U.S. Cl.
CPC ..................................... *B01J 2/30* (2013.01); *B01F 9/02* (2013.01); *B01J 8/008* (2013.01); *B01J 8/0045* (2013.01);
(Continued)

(58) Field of Classification Search
CPC ....... B01F 9/00; B01F 9/02; B01J 2/00; B01J 2/30; B01J 8/00; B01J 8/0015;
(Continued)

(56) References Cited

U.S. PATENT DOCUMENTS 6,812,201 B1 * 11/2004 Weuthen .............. C11D 3/0026
510/353
6,918,976 B2 * 7/2005 Sato ........................ C06B 29/22
149/19.1
(Continued)

FOREIGN PATENT DOCUMENTS

EP    1788594 B1    4/2017
FR    2721900 A1    1/1996
(Continued)

OTHER PUBLICATIONS

Machine translation of FR 2829107 A1, which was published on Mar. 3, 2003. (Year: 2020).*
(Continued)

*Primary Examiner* — Natasha E Young
(74) *Attorney, Agent, or Firm* — Millen White Zelano and Branigan, PC; John Sopp (57) ABSTRACT

The invention relates to a pretreatment process for improving the filling of a chamber with solid particles, in which said solid particles are mixed before loading of said solid particles into the chamber with at least one lubricant that is solid at ambient temperature chosen from saturated fatty acids having 14 or more carbon atoms, metal salts of saturated fatty acids having 14 or more carbon atoms, esters of fatty
(Continued)

acids having 14 or more carbon atoms, fatty alcohols having 14 or more carbon atoms, linear N-alkanes having 16 or more carbon atoms in solid form, fumaric acid, talc, sodium stearoyl fumarate, the lubricant being introduced at a content of between 0.01% and 1% relative to the total weight of the mixture of solid particles and lubricant. The invention also relates to the use of the process for the pretreatment of particles of adsorbents for the separation of xylenes.

17 Claims, 4 Drawing Sheets (51) Int. Cl.
*B01J 8/00* (2006.01)
*B01F 9/00* (2006.01)
*B01F 9/02* (2006.01)
*C10M 105/36* (2006.01)
*C07C 7/12* (2006.01)
*C07C 15/08* (2006.01)
*C10N 50/08* (2006.01)

(52) U.S. Cl.
CPC ............ *C10M 105/36* (2013.01); *C07C 7/12* (2013.01); *C07C 15/08* (2013.01); *C10N 2050/08* (2013.01)

(58) Field of Classification Search
CPC ........... B01J 8/0045; B01J 8/008; C07C 7/00; C07C 7/12; C07C 15/00; C07C 15/02; C07C 15/067; C07C 15/08; C10M 105/00; C10M 105/08; C10M 105/32; C10M 105/36; C10N 2050/00; C10N 2050/08

See application file for complete search history.

(56) References Cited

U.S. PATENT DOCUMENTS

| | | |
|---|---|---|
| 7,878,428 B2 | 2/2011 | Pinon et al. |
| 7,927,555 B2 | 4/2011 | Petzoldt et al. |
| 8,530,367 B2 | 9/2013 | Bouvier et al. |
| 8,545,641 B2 | 10/2013 | Sagawa et al. |

FOREIGN PATENT DOCUMENTS

| | | | |
|---|---|---|---|
| FR | 2829107 A1 * | 3/2003 | ........... B65G 11/066 |
| FR | 2872497 A1 | 1/2006 | |
| FR | 2903978 A1 | 1/2008 | |
| JP | 2009016849 A | 1/2009 | |
| WO | 06094766 A1 | 9/2006 | |

OTHER PUBLICATIONS

International Search report in PCT/2018EP/083126 dated Apr. 2, 2019 (pp. 1-15).

* cited by examiner

PRETREATMENT PROCESS FOR IMPROVING THE FILLING OF A CHAMBER WITH SOLID PARTICLES

This application is a national stage application claiming priority to PCT/EP2018/083126, now WO 2019/120938, filed on Nov. 30, 2018, which claims priority to French Patent Application Serial No. FR1762784, filed on Dec. 21, 2017.

FIELD OF THE INVENTION

The invention relates the field of the filling of reactors with solid particles. The invention relates more particularly to the loading of chemical or electrochemical, petroleum or petrochemical fixed-bed reactors with solid particles in the divided state, which may be in the form of beads, grains, cylinders, pellets, rods or any other shape, but which are generally of relatively small dimensions. The particles may in particular be adsorbents, molecular sieves, or grains of solid catalysts, which are generally extruded, produced either in an irregular shape, or in the shape of single-lobed or multilobed rods, the dimensions of which vary depending on the case, from a few tenths of millimetres to a few centimetres.

PRIOR ART

Most industrial conversion or separation processes involve the use of a solid used in a reactor. The performances of these processes are in general directly proportional to the number of active sites or adsorption sites present in the reactor. It is therefore desirable to load the reactor as densely as possible. A person skilled in the art is for example aware of "sock loading", which consists in manually pouring the solid particles with the aid of a flexible hose, referred to as a sleeve or sock. High-density loading techniques also exist, for example the Catapac™ high-density loading technique described in patent application FR2721900 A1, that makes it possible to achieve a loading density at least 10% greater than sock loading.

For a long time lubricants in solid form have been used in the pharmaceutical industry, cosmetics industry, agri-food industry and petrochemical industry (PVC, etc.) for the purpose of improving the fluidity of the mixtures of powders, which is a critical property for many processes. For example, in the pharmaceutical industry, granules must pass through a feed hopper before arriving in the mould which will give them the shape of a tablet. The passage through this hopper must be as fluid as possible in order to guarantee that tablets with homogeneous masses are obtained. In order to do this, almost all pharmaceutical process have integrated a preliminary step of mixing the granules with a lubricant.

The increase in the fluidity of the powders is made possible owing to the lubricant which will be distributed on the surface of the granules. Owing to the presence of a lubricant film formed on the surface, the distance between the granules increases and enables, firstly, a reduction in the inter-particle adhesion forces.

However, when the amount of lubricant increases too significantly, clusters are formed at the surface which increases the surface roughness and creates friction between the particles. The opposite effect to the one desired is then observed: the adhesion force increases.

There is therefore an optimum which depends on the size of the solid particles and on the nature thereof, since these parameters control the inter-particle adhesion forces.

Industrial lubricants are generally composed of long carbon-based chains (at least 14 carbon atoms) associated with a functional group at the chain end such as carboxylic acid (—COOH), their associated salts (—COO—Na+), alcohol (—OH) or ester (—COOR).

Figure 1:
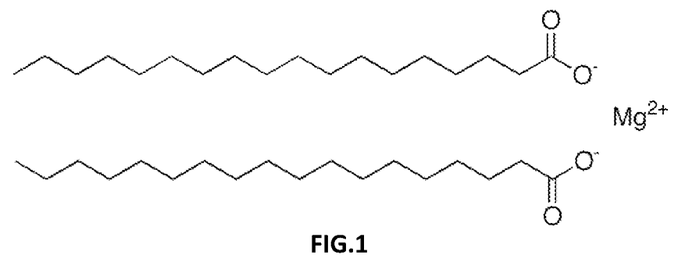
FIG. 1 represents the structural chemical formula of magnesium stearate.

The most used lubricant is magnesium stearate, the formula of which is clarified by FIG. 1, the biocompatibility of which is useful in pharmaceutical tablets, the agri-food industry and cosmetics.

These lubricants are generally added to the powder mixtures with a solid-solid mixing step. This type of mixing is far from common and constitutes a crucial step for achieving the desired performances. The lubricant must be distributed homogeneously on the surface, without forming clusters, in order to effectively reduce the inter-particle adhesion forces.

Within the context of filling reactors, to date catalysts or adsorbents in the form of solid particles are conveyed in the form of large transport bags or barrels to site. As indicated previously, there are then several methods of loading, the main ones are:

- manual sock loading, which consists in manually decanting the solid particles, for example using a sleeve or flexible hose;
- loading with the aid of a device internal to the chamber, such as Catapac™ described in patent FR2721900, which makes it possible to load at least 10% more densely and more homogeneously than sock loading. This loading technique is based in particular, owing to the hollow configuration of a rotary shaft, on the introduction and/or withdrawal of a functional device into/from the chamber during loading. The device introduced is a device comprising, in its upper part, a means for feeding with particles and, in its base located inside the chamber to be loaded, a dispersion system attached to a central shaft rotated about a substantially vertical axis by a motor means, and a feed pipe at least partially surrounding the central shaft, said central shaft is a tube having an internal diameter sufficient to make it possible to carry out, in the zone to be loaded, by means of this tube and during the loading period, a certain number of operations connected or complementary to said loading operation, this device comprising a stationary tube attached to the feed pipe and placed inside said rotary central shaft, the stationary tube and said rotary central shaft being substantially coaxial.

However, there remains a need for improvement in the techniques for filling reactors with solid particles in order to improve the performances of the processes carried out in these reactors.

Surprisingly, it has specifically been discovered that, under certain conditions, the addition of a lubricant to the solid particles leads to an increase in the filling densities of the reactors. The invention thus proposes a pretreatment process which comes upstream of the loading, whether it is a manual sock loading or a high-density loading, and which makes it possible to improve the filling of the reactors.

SUBJECT OF THE INVENTION

The invention relates to a pretreatment process for improving the filling of a chamber with solid particles. The chamber may be any catalytic reactor or any adsorber, requiring a dense loading of solid particles of catalysts or of adsorbents, known to a person skilled in the art.

The invention also relates to the pretreated solid particles obtained.

The invention lastly relates to the use of the pretreatment process according to the invention for filling a catalytic or adsorption reactor, in particular for a xylene separation process.

SUMMARY OF THE INVENTION

The invention relates to a pretreatment process for improving the filling of a chamber with solid particles, in which said solid particles are mixed before loading of said solid particles into the chamber with at least one lubricant that is solid at ambient temperature chosen from saturated fatty acids having 14 or more carbon atoms, metal salts of saturated fatty acids having 14 or more carbon atoms, esters of fatty acids having 14 or more carbon atoms, fatty alcohols having 14 or more carbon atoms, linear N-alkanes having 16 or more carbon atoms in solid form, fumaric acid, talc, sodium stearoyl fumarate, the lubricant being introduced at a content of between 0.01% and 1% relative to the total weight of the mixture of solid particles and lubricant.

In one embodiment, the loading is carried out manually with the aid of a flexible hose.

In another embodiment, the loading is carried out with the aid of a functional device internal to the chamber which may be introduced into and/or withdrawn from said chamber.

Preferably, said internal functional device comprises, in its upper part, a means for feeding with particles and, in its base located inside the chamber to be loaded, a dispersion system attached to a central shaft rotated about a substantially vertical axis by a motor means, and a feed pipe at least partially surrounding the central shaft, said central shaft is a tube having an internal diameter sufficient to make it possible to carry out, in the zone to be loaded, by means of this tube and during the loading period, a certain number of operations connected or complementary to said loading operation, this device comprising a stationary tube attached to the feed pipe and placed inside said rotary central shaft, the stationary tube and said rotary central shaft being substantially coaxial.

Preferably, the lubricant content is between 0.01% and 0.5% by weight, very preferably between 0.05% and 0.25% by weight.

Preferably, the lubricant is a fatty acid chosen from myristic acid, palmitic acid, stearic acid, arachidic acid, behenic acid, lignoceric acid or cerotic acid, or a metal salt of saturated fatty acids having 14 or more carbon atoms, chosen from salts based on aluminium, calcium, magnesium, zinc, sodium, barium or lithium, a fatty alcohol having 14 or more carbon atoms chosen from myristyl alcohol, palmityl alcohol or stearyl alcohol, a paraffin having 16 or more carbon atoms, an ester of saturated fatty acids having 14 or more carbon atoms chosen from the following compounds: glyceryl monostearate, glyceryl distearate, glyceryl monopalmitate, glyceryl dipalmitate, glyceryl tristearate, glyceryl tripalmitate, glyceryl trimyristate or glyceryl tribenhenate.

Very preferably, the lubricant is chosen from magnesium stearate, calcium stearate and barium stearate.

More preferably still, the lubricant is magnesium stearate.

Advantageously, the solid particles are particles of catalysts or particles of adsorbents.

The solid particles may be in the form of beads or extrudates.

Preferably, the equivalent diameter of the solid particles is less than 2 mm.

Advantageously, the particles of lubricant used have a particle size such that at least 90% by weight of the particles of lubricant pass through a 90 µm screen.

Preferably, the mixing is carried out at ambient temperature and atmospheric pressure in a drum-type mixer.

Very preferably, the mixing is carried out with a speed of rotation of between 5 and 30 rpm, for a time of between 5 min and 20 min, and with a degree of filling in the tank of the mixer of between 30% and 80%.

Preferably, the chamber is a chemical or electrochemical, petroleum or petrochemical type reactor.

The invention also relates to the use of the pretreatment process for the pretreatment of particles of adsorbents for the separation of xylenes.

BRIEF DESCRIPTION OF THE DRAWINGS

FIGS. 1 to 4 illustrate the invention in a nonlimiting manner.

DETAILED DESCRIPTION OF THE INVENTION

The ranges of values are understood, unless otherwise indicated, as limits included.

The pretreatment process according to the invention consists in mixing the solid particles (for example in the form of beads or extrudates) with a lubricant that is solid at ambient temperature before the step of loading the particles into the reaction chamber in order to densify the beds of particles even more. Without wishing to be tied to any one theory, it appears that the lubricant, if it is introduced under suitable conditions, then enables a reduction in the interparticle adhesion forces that leads to a better quality filling. The effect observed is attributed to the fact that the filling of the reactors is governed by the same physical phenomenon that is involved in the increase in the fluidity, namely the adhesion force between the particles. Specifically, when the adhesion force is low relative to the force of gravity experienced by the particle, the solid particle is easily "arranged" and the filling is of good quality. Conversely, when the adhesion force is large compared to gravity, the solid particle has a greater tendency to agglomerate with the neighbouring particles, creating empty spaces and a poor-quality filling.

According to the invention, the proposed pretreatment process makes it possible to improve the filling of a reactor with solid particles, by mixing the solid particles (beads or extrudates for example) with a lubricant that is solid at ambient temperature before the step of loading (manual loading or loading with the aid of a functional device). The lubricant present around the solid particles is then discharged in the process during the start-up of the process carried out in the reactor.

On the industrial scale, the pretreatment process according to the invention may take place at two moments, either on site, just before the loading into the reactor, or at the end of the process for preparing the solid particles (for example of adsorbent or of catalyst), once the shaping is finished and before the particles are sent to site. The second embodiment may make it possible to reduce the transport costs due to the better compaction in the bags of the particles and to avoid making the start-up procedures more complex.

The lubricant used in the pretreatment process according to the invention is solid at ambient temperature and is chosen from the following compounds:
  saturated fatty acids having 14 or more carbon atoms;
  metal salts of saturated fatty acids having 14 or more carbon atoms;
  esters of fatty acids having 14 or more carbon atoms;
  fatty alcohols having 14 or more carbon atoms;
  linear N-alkanes (paraffins) having 16 or more carbon atoms in solid form;
  other compounds such as fumaric acid, talc, sodium stearoyl fumarate.
Preferably:
Saturated fatty acids having 14 or more carbon atoms are chosen from myristic acid, palmitic acid, stearic acid, arachidic acid, behenic acid, lignoceric acid or cerotic acid.
Metal salts of saturated fatty acids having 14 or more carbon atoms are chosen from in particular salts based on aluminium, calcium, magnesium, zinc, sodium, barium, lithium, etc.
Fatty alcohols having 14 or more carbon atoms are chosen from the following alcohols: myristyl alcohol, palmityl alcohol or stearyl alcohol.
Linear N-alkanes are paraffins having 16 or more carbon atoms in solid form.
Esters of saturated fatty acids having 14 or more carbon atoms are chosen from the following compounds: glyceryl monostearate, glyceryl distearate, glyceryl monopalmitate, glyceryl dipalmitate, glyceryl tristearate, glyceryl tripalmitate, glyceryl trimyristate or glyceryl tribenhenate.

Among the preferred lubricant compounds according to the invention, salts of magnesium stearate, calcium stearate and barium stearate type are preferred. Very preferably, magnesium stearate is used (FIG. 1).

The lubricants above may be used alone or as a mixture.

The lubricant used in the pretreatment process according to the invention advantageously has a fine particle size and preferably at least 90% by weight of the sample must be able to pass through a 90 μm screen. More particularly, the particle size of the lubricant is such that the size of the particles of lubricant is less than 90 μm.

The chosen particle size makes it possible to obtain an optimal distance between the solid particles.

The solid particles (for example of adsorbent or of catalyst) to be loaded into the chamber preferably have an equivalent diameter of less than 2 mm.

Preferably, said solid particles are substantially spherical.

The composition by weight of lubricant in the mixture formed by the lubricant and the solid particles must be suitable for having the desired effect. In the case of an excessive concentration of lubricant, the particles of lubricant form clusters at the surface of the particles, leading to excessively large distances and a loss of the desired effect. Scanning electron microscopy shows that the surface of the particles is completely covered starting from 1% by weight of the lubricant and that clusters are formed beyond this content.

The weight content of lubricant in the mixture formed by the lubricant and the solid particles is between 0.01% and 1% by weight, preferably between 0.01% and 0.5% by weight, more preferably between 0.01% and 0.25% by weight, limits included, relative to the total weight of the mixture formed by the lubricant and the solid particles.

The mixing is advantageously carried out at ambient temperature and atmospheric pressure in a drum-type mixer in order to maximize the diffusion mechanisms, which mixing consists of an individual displacement of the particles so that the lubricant can be moved and distributed homogeneously at the surface of the beads.

As is known to a person skilled in the art (see in particular H. Berthiaux, "Mélange et homogénéisation de solides divisés" [Mixing and homogenization of divided solids], Technique de l'ingénieur, J3397 V1 (2002)), in this type of mixing, speeds of rotation ranging from 5 to 30 rpm over a time ranging from 5 min to 20 min and with degrees of filling in the tank of the mixer of from 30% to 80% are favoured. The mixing is carried out by the rotation of the tank with a conical shape. The conical shape of the mixer advantageously ensures a radial homogenization.

The gains relative to loading using a high-density loading device, for example of Catapac™ type, are evaluated by measuring the tapped filling densities (TFDs). The analysis is carried out by weighing the mass of solid particles introduced into a given volume after compaction (2400 taps). The tapped density represents a "maximized" filling which in general is not completely achieved by a high-density industrial loading. However, the Catapac™ behaviour remains close to the TFD results and the industrial densities are extrapolated from these TFD tests. This tapped filling density method is therefore an indicator that is consistent with the Catapac™ filling performance.

The gains relative to manual loading, for example a sock loading, are evaluated by measuring the poured densities. The analysis is carried out by weighing the mass of solid particles introduced into a given volume (without compaction). The poured density is considered to be equivalent to that obtained at the end of a manual loading since it results from the same flow.

These two methods therefore allow an estimation of the densities obtained on the industrial scale.

Moreover, when the conditions mentioned above are combined, the pretreatment process according to the invention advantageously enables an increase in the filling densities by manual loading using a flexible hose that may range up to 4% and an increase in the filling densities with an internal device, for example Catapac™, ranging from 0 to 4%.

In addition to the gain provided to the application process (catalytic process or adsorption process) inherent to the increase in the number of catalytic and/or adsorption sites in the reactor, the following are observed:
  A reduction in the re-compaction effect. A re-compaction is often observed several hours after the start-up of the unit which corresponds to a density increase of 1 to 2%. This effect creates an empty space after loading on top of the beds which may be detrimental to the performance. The pretreatment step according to the invention makes it possible to reduce, or even to completely eliminate, this effect of compaction after start-up of the unit.

Better hydrodynamics in the reactor. The increase in filling density expresses a more homogeneous filling which will reduce the hydrodynamic dispersion.

A facilitated operation of the loading device, in particular for internal devices of Catapac™ type, owing to the increase in the fluidity of the solid induced by the pretreatment step.

It has also been observed that the pretreated solid particles have a reduction in the water uptake in the case of hygroscopic solid particles. The hydrophobic film present on the surface protects them from moisture and a reduction in the static electricity generated during the flow.

EXAMPLES

Example 1: Loading of Adsorbent for the Separation of Xylenes

The separation of xylenes is carried out by an adsorbent of X zeolite type in the form of beads having a nominal diameter of 0.54 mm and which are loaded by a Catapac™ type loading into the adsorber. The industrial densities are extrapolated from the tapped densities (TFD).

Three types of lubricants were tested: magnesium stearate, calcium stearate and barium stearate.

Pretreatment

In the laboratory, the adsorbent was mixed with the lubricant by rotation of a drum-type mixer.

The drum is slightly inclined so as to ensure a radial homogenization.

The operating procedure followed is the following:
Introduction of the adsorbent into the drum, the amount of adsorbent being around 50 g
Introduction of the lubricant into the drum, in suitable proportions (between 0 and 1% by weight relative to the weight of the adsorbent)
Rotation of the drum at a speed of 10 rpm for 10 min
Measurement of the tapped density, as described above.
Measurement of the poured density, as described above.

The water content is determined at the start by a measurement of the loss on ignition in % by weight (LOI) at 900° C. then the mass of the sample is measured between each step, so as to know the exact mass of water taken up during the pretreatment test. The tests are carried out in a laboratory having a controlled hygrometry equal to 55%. The results are expressed as mass of dry adsorbent per unit volume, which is the relevant value for the process, by correcting the mass of lubricated adsorbents introduced during the density measurement, with respect to the water and lubricant content thereof.

Figure 2A:
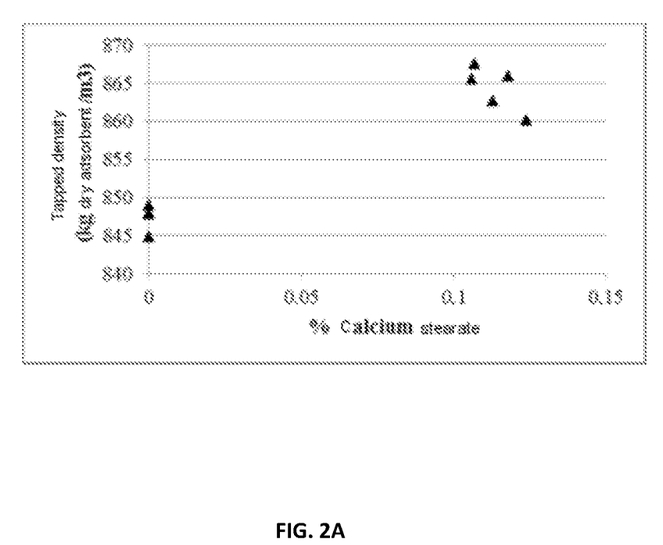
FIGS. 2A, 2B, 2C relate to Example 1 and represent the change in the tapped density in kg of dry adsorbant/m$^3$ relative to the lubricant content in % by weight relative to the total weight of the mixture, for three types of lubricants: calcium stearate, magnesium stearate and barium stearate.
Figure 2B:
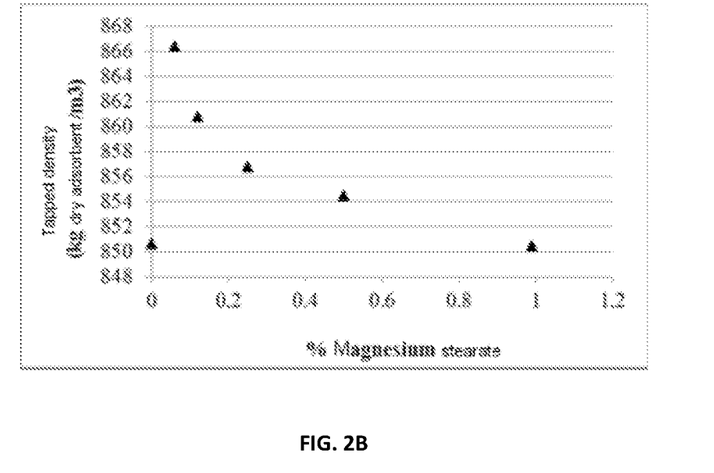
Figure 2C:
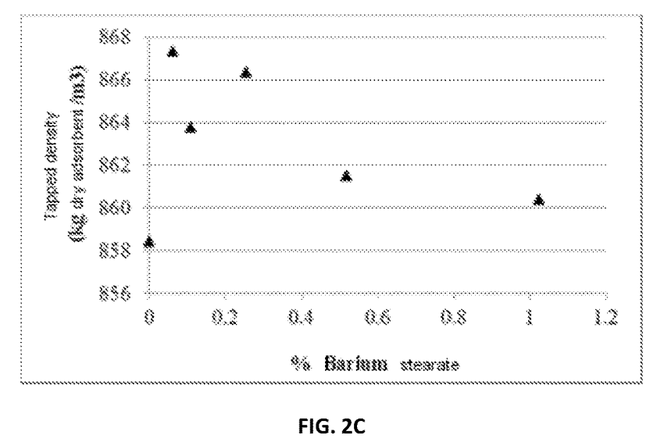

The tapped density results for three different lubricants (magnesium stearate, calcium stearate and barium stearate) are depicted by FIGS. 2A, 2B and 2C. The composition of the mixture is expressed as a percentage by weight. The points at 0% constitute the (comparison) reference, i.e. the tapped filling density of the adsorbent alone, and therefore without mixing with the lubricant.

The results obtained with calcium stearate (FIG. 2A) show a satisfactory reproducibility and prove that the pretreatment enables a significant improvement in the tapped density.

The tests carried out with barium stearate and magnesium stearate show an increase in tapped density for all lubricant contents between 0.01% and 1% relative to the weight of mixture and reveal an optimum for lubricant contents of between 0.05% and 0.25% relative to the weight of mixture. This behaviour is in agreement with the theory set out above which anticipates a reduction in the adhesion force firstly then a reversal of the phenomenon when the lubricant begins to cluster on the surface, creating roughness rather than the reduction in the interaction forces.

Under optimal conditions, the pretreatment process according to the invention thus enables a gain in tapped density of 2.2% compared to the reference.

Figure 3A:
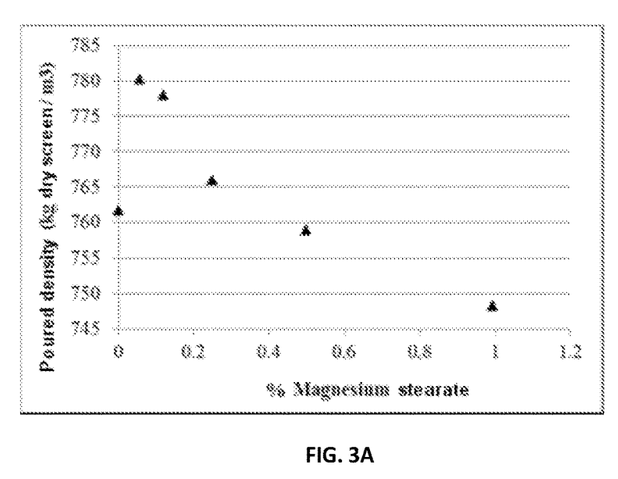
FIGS. 3A and 3B relate to Example 1 and represent the change in the poured density in kg of dry adsorbant/m$^3$ relative to the lubricant content in % by weight relative to the total weight of the mixture, for two types of lubricants: magnesium stearate and barium stearate.
Figure 3B:
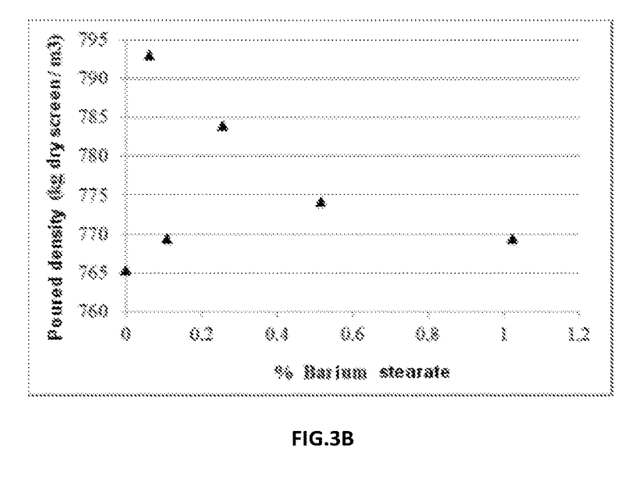

The results of the poured density are expressed in the same way and are presented by FIGS. 3A (with magnesium stearate) and 3B (with barium stearate).

The effect of the lubricant on the poured density is identical to that observed on the tapped density with an increase in the poured density that ranges up to 3.7% compared to the reference.

This result confirms that the pretreatment process improves both a conventional manual sock-type loading (poured density) and a high-density loading of Catapac™ type (tapped density).

Figure 4:
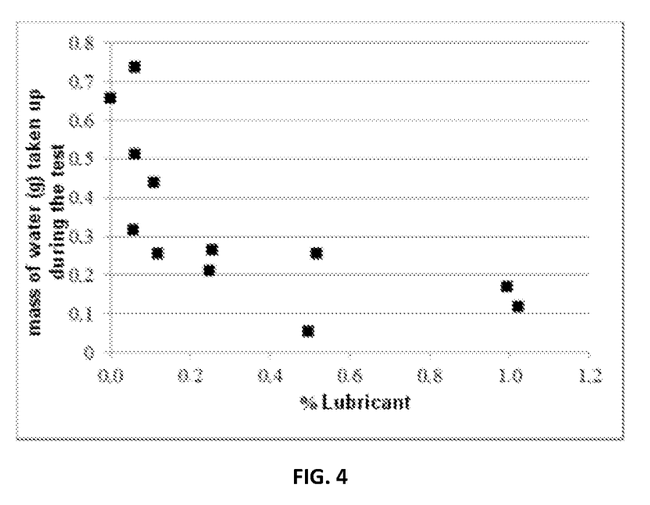
FIG. 4 relates to Example 1 and represents the water uptake in grams of a sample of adsorbent pretreated with magnesium stearate in accordance with the invention, as a function of the lubricant content in % by weight relative to the total weight of the mixture.

Furthermore, the measurement of the water uptake during the tests demonstrates a protective role of the lubricant with respect to moisture, as represented by FIG. 4 which shows the mass of water in grams taken up by the pretreated adsorbent sample as a function of the lubricant content by weight relative to the total weight of mixture.

During the start-up of a unit, in the absence of an adsorbent pretreatment process, the transport bags are weighed on site and those having an excessively high water uptake are pronounced "out of specification" and are not loaded. The use of a pretreatment according to the invention upstream of the transport may therefore also make it possible to limit the effect of the water uptake and thus avoid a loss before loading.

Finally, it has been observed that the lubricant has non-stick properties and greatly reduces the generation of static electricity. The passage of a non-pretreated adsorbent into the drum leads to the adhesion of the particles on the wall. A comparison of the content of the drum after 10 minutes of rotation at 10 rpm, respectively for the non-pretreated adsorbent and for the adsorbent-lubricant mixture with a content equal to 1% of magnesium stearate, shows the particles adhere to the wall with the non-pretreated adsorbent but do not adhere with the adsorbent-lubricant mixture.

The presence of the lubricant inhibits this phenomenon of generating static electricity and enables easier handling of the solid.

Example 2: Breakthrough Test

The absence of interactions of the pretreatment process according to the invention with the performances of a xylene separation process has been verified by breakthrough (frontal chromatography) tests as described in patent FR2903978, carried out on a reference column comprising adsorbent (comparison) and a pretreated column comprising adsorbent pretreated with 0.8% of calcium stearate by weight relative to the total weight of the mixture (according to the invention). The amount of adsorbent used for these tests is around 75 g.

The operating procedure is the following:
In the case of the pretreated column, mixing with 0.8% calcium stearate, according to the methodology described in Example A.
Filling the column with the pretreated or non-pretreated adsorbent and installing in the test bed.
Filling with the solvent (para-diethylbenzene at ambient temperature).

Gradual increase to the adsorption temperature under a stream of solvent (5 cm³/min). In the case of the pretreated column, samples of para-diethylbenzene are withdrawn every 2 minutes during the temperature increase.

Injection of solvent when the adsorption temperature is reached.

Solvent/feedstock permutation to inject the feedstock.

Injection of the feedstock is then maintained for a time sufficient to reach thermodynamic equilibrium.

Collection and analysis of the breakthrough effluent.

The operation is carried out at a feedstock flow rate of 10 cm³/min.

The pressure is sufficient for the feedstock to remain in the liquid phase, i.e. 1 MPa. The adsorption temperature is 175° C. The composition of the feedstock is the following:

meta-xylene: 45% by weight
para-xylene: 45% by weight
iso-octane: 10% by weight (the latter is used as tracer for estimating non-selective volumes and is not involved in the separation).

During the temperature increase of the pretreated column, the samples withdrawn at around 120-130° C. become two-phase samples. This phenomenon is attributed to the melting of the lubricant (its melting point is 130° C.) which is then carried along by the para-diethylbenzene.

The results from the analysis of the breakthrough curves are summarized in Table 1.

TABLE 1

Results of the breakthrough curves

| | Reference Column (comparison) | Pretreated Column (according to the invention) |
|---|---|---|
| Loss on ignition at 900° C. | 5.5% | 5.5% |
| Para-xylene/meta-xylene selectivity (1) | 1 | 1.003 |
| Capacity (1) | 1 | 0.995 |
| Theoretical plate height (1) | 1 | 1.011 |

(1) The results are expressed in relative terms with respect to the reference column, i.e. by dividing the value obtained by the value obtained with the reference column.

It is observed that the pretreatment has no impact on the gross performance of the adsorbent. These results confirm the absence of interactions with the performance of the process and confirm the departure of the lubricant with the solvent (here para-diethylbenzene) during the start-up of the xylene adsorption unit.

Consequently, the example shows that the application of the pretreatment process according to the invention to the loading of an adsorbent into a xylene separation process makes it possible to improve the density of Catapac™ dense loading by 2.2%, without adversely affecting the performance of the adsorbant, which results in an increase in the productivity of the process of 2.2% (proportional to the mass of adsorbent present in the reactor).

The pretreatment process tested within the context of the separation of xylenes enables an increase in the tapped and poured densities of 2% to 4%, without adversely affecting the performance of the adsorbent. Given that the industrial densities are extrapolated from the tapped densities and that the performances are proportional to the mass of adsorbent present in the reactor, the pretreatment process according to the invention single-handedly enables an increase in productivity of 2% to 4% for the xylene separation process.

Advantages of the Process According to the Invention

Besides the gain in loading density of the solid particles, the process for pretreatment of solid particles according to the invention also enables:

a reduction in the re-compaction effect of the beds after the start-up
a reduction in the hydrodynamic dispersion
a facilitated operation of the loading due to the improved fluidity
a reduction in the water uptake of the solid particles
a reduction in the static electricity generated during the flow.

Applications

The pretreatment process according to the invention applies to any type of solid particles and may thus be used in any type of catalytic or adsorption process using a bed of adsorbents, catalysts or solid particles.

The pretreatment process according to the invention applies more particularly to the loading of adsorbents for the implementation of a xylene separation process, for example the ELUXYL™ process. Irrespective of the type of loading, the pretreatment process tested within the context of the separation of xylenes enables a significant increase in the loading density, without adversely affecting the intrinsic performance of the adsorbent. Since the performance of the xylene separation process is proportional to the mass of adsorbent present in the reactor, the pretreatment process according to the invention single-handedly enables an increase in productivity of the xylene separation process.

The invention claimed is:

1. A pretreatment process for improving the filling of a chamber with solid particles, comprising mixing said solid particles, before loading of said solid particles into the chamber, with at least one lubricant that is solid at ambient temperature chosen from saturated fatty acids having 14 or more carbon atoms, metal salts of saturated fatty acids having 14 or more carbon atoms, esters of fatty acids having 14 or more carbon atoms, fatty alcohols having 14 or more carbon atoms, linear N-alkanes having 16 or more carbon atoms in solid form, fumaric acid, talc or sodium stearoyl fumarate, the lubricant being introduced at a content of between 0.01% and 1% relative to the total weight of the mixture of solid particles and lubricant, and then loading the solid particles mixed with lubricant into the chamber, the loading being carried out manually with the aid of a flexible hose or the loading being carried out with the aid of a functional device internal to the chamber which may be introduced into and/or withdrawn from said chamber.

2. The process according to claim 1, wherein the loading is carried out manually with the aid of a flexible hose.

3. The process according to claim 1, wherein the loading is carried out with the aid of a functional device internal to the chamber which may be introduced into and/or withdrawn from said chamber.

4. The process according to claim 3, wherein the functional device internal to the chamber comprises, in an upper part, a means for feeding with particles and, in a base located inside the chamber to be loaded, a dispersion system attached to a central shaft rotated about a substantially vertical axis by a motor means, and a feed pipe at least partially surrounding the central shaft, said central shaft is a tube having an internal diameter sufficient to make it possible to carry out, in the zone to be loaded, by means of this tube and during the loading period, a certain number of operations connected or complementary to said loading operation, this device comprising a stationary tube attached to the feed pipe and placed inside said rotary central shaft, the stationary tube and said rotary central shaft being substantially coaxial.

5. The process according to claim 1, wherein the lubricant content is between 0.01% and 0.5% by weight.

6. The process according to claim 5, wherein the lubricant content is between 0.05% and 0.25% by weight.

7. The process according to claim 1, wherein the lubricant is a fatty acid chosen from myristic acid, palmitic acid, stearic acid, arachidic acid, behenic acid, lignoceric acid or cerotic acid, or a metal salt of saturated fatty acids having 14 or more carbon atoms, chosen from salts based on aluminium, calcium, magnesium, zinc, sodium, barium or lithium, a fatty alcohol having 14 or more carbon atoms chosen from myristyl alcohol, palmityl alcohol or stearyl alcohol, a paraffin having 16 or more carbon atoms, an ester of saturated fatty acids having 14 or more carbon atoms chosen from the following compounds: glyceryl monostearate, glyceryl distearate, glyceryl monopalmitate, glyceryl dipalmitate, glyceryl tristearate, glyceryl tripalmitate, glyceryl trimyristate or glyceryl tribenhenate.

8. The process according to claim 1, wherein the lubricant is chosen from magnesium stearate, calcium stearate and barium stearate.

9. The process according to claim 8, wherein the lubricant is magnesium stearate.

10. The process according to claim 1, wherein the solid particles are particles of catalysts or particles of adsorbents.

11. The process according to claim 1, wherein the solid particles are in the form of beads or extrudates.

12. The process according to claim 1, wherein the equivalent diameter of the solid particles is less than 2 mm.

13. The process according to claim 1, wherein the lubricant is in the form of particles which have a particle size such that at least 90% by weight of the particles of lubricant pass through a 90 µm screen.

14. The process according to claim 1, wherein the mixing is carried out at ambient temperature and atmospheric pressure in a drum-type mixer.

15. The process according to claim 14, wherein the mixing is carried out with a speed of rotation of between 5 and 30 rpm, for a time of between 5 min and 20 min, and with a degree of filling in the tank of the mixer of between 30% and 80%.

16. The process according to claim 1, wherein the chamber is a chemical or electrochemical, petroleum or petrochemical reactor.

17. A process for the pretreatment of particles of adsorbents and for the separation of xylenes comprising conducting the process of claim 1 and contacting the resulting particles with xylenes.

* * * * *